United States Patent
Lee et al.

(10) Patent No.: US 10,302,547 B2
(45) Date of Patent: May 28, 2019

(54) PARTICLE SENSING DEVICE

(71) Applicant: LG INNOTEK CO., LTD., Seoul (KR)

(72) Inventors: Ho Min Lee, Seoul (KR); Dong Mug Seong, Seoul (KR); Eun Jung Jeon, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 0 days.

(21) Appl. No.: 15/760,114

(22) PCT Filed: Jan. 4, 2017

(86) PCT No.: PCT/KR2017/000072
§ 371 (c)(1),
(2) Date: Mar. 14, 2018

(87) PCT Pub. No.: WO2017/119703
PCT Pub. Date: Jul. 13, 2017

(65) Prior Publication Data
US 2018/0252631 A1  Sep. 6, 2018

(30) Foreign Application Priority Data

Jan. 6, 2016 (KR) .................. 10-2016-0001481

(51) Int. Cl.
*G01N 15/06* (2006.01)
*G01N 15/14* (2006.01)
(Continued)

(52) U.S. Cl.
CPC ..... *G01N 15/1434* (2013.01); *G01N 15/0205* (2013.01); *G01N 15/06* (2013.01);
(Continued)

(58) Field of Classification Search
CPC ........... G01N 21/9501; G01N 15/1459; G01N 21/94; G01N 21/47; G01N 15/0205;
(Continued)

(56) References Cited

U.S. PATENT DOCUMENTS 5,105,093 A * 4/1992 Niwa .................. G01N 15/0211
250/214 C
5,432,605 A * 7/1995 Naqwi .................. G01B 11/105
356/485
(Continued)

FOREIGN PATENT DOCUMENTS

KR       20-0367121 Y1   11/2004
KR    10-2012-0052455     5/2012
(Continued)

OTHER PUBLICATIONS

International Search Report (with English Translation) and Written Opinion dated Mar. 13, 2017 issued in Application No. PCT/KR2017/000072.

*Primary Examiner* — Michael P Stafira
(74) *Attorney, Agent, or Firm* — KED & Associates LLP

(57) ABSTRACT

A particle sensing device is provided. The particle sensing device may include a light emitter configured to emit and output light into a light scattering space, and a light receiver provided in a maximum light scattering angle region. A maximum intensity of scattered light formed when the light emitted from the light emitter is scattered by a particle in the light scattering space may be obtained in the maximum light scattering angle region, and the light receiver may be configured to receive the scattered light incident thereon and generate a photocurrent signal.

15 Claims, 12 Drawing Sheets

(51) Int. Cl.
*G01N 21/53* (2006.01)
*H01L 51/42* (2006.01)
*H01L 51/44* (2006.01)
*G01N 15/02* (2006.01)
G01N 15/00 (2006.01)
H01L 51/00 (2006.01)

(52) U.S. Cl.
CPC ......... *G01N 21/53* (2013.01); *H01L 51/4246* (2013.01); *H01L 51/4253* (2013.01); *H01L 51/442* (2013.01); *G01N 2015/0046* (2013.01); *G01N 2015/0693* (2013.01); *G01N 2015/1493* (2013.01); *G01N 2201/0642* (2013.01); *H01L 51/0036* (2013.01); *H01L 51/0037* (2013.01); *H01L 51/0047* (2013.01); *H01L 51/448* (2013.01)

(58) Field of Classification Search
CPC .... G01N 21/21; G01N 15/1434; G01N 21/49; G01N 21/8806; G01N 2015/1493; G01N 21/53; G01N 15/0211; G01N 15/1463; G01N 2015/1497; G01N 2021/8825; G01N 2201/06113; G01N 15/1436; G01N 21/474; G01N 2015/1452; G01N 2015/1486; G01N 2015/149; G01N 2021/6469; G01N 2021/8845; G01N 2021/8848; G01N 21/956; G01N 2201/065; G01N 2015/0088; G01N 2021/8874; G01N 21/51; G01N 21/645; G01N 21/6486; G01N 2015/025; G01N 2021/4707; G01N 2021/8861; G01N 2021/95676; G01N 21/64; G01N 21/65; G01N 15/06; G01N 15/10; G01N 2015/0065; G01N 2015/0222; G01N 2015/0693; G01N 2015/1087; G01N 2015/1093; G01N 2021/4709; G01N 2021/6421; G01N 21/88; G01N 15/14; G01N 2015/0046; G01N 2015/0294; G01N 2015/1075; G01N 2015/144; G01N 2015/145; G01N 2021/6419; G01N 21/01; G01N 21/0303; G01N 21/658; G01N 2201/064; G01N 2201/068; G01N 33/18; G01N 15/1427; G01N 2015/0038; G01N 2015/03; G01N 2015/1402; G01N 2021/4726; G01N 2021/6417; G01N 2021/6467; G01N 2021/6482; G01N 2021/6484; G01N 2021/653; G01N 2021/8592; G01N 21/23; G01N 21/4738; G01N 21/554; G01N 21/6445; G01N 21/6458; G01N 21/648; G01N 21/84; G01N 21/85; G01N 21/95; G01N 2201/0637; G01N 15/1468; G01N 15/147; G01N 1/2211; G01N 2001/2223; G01N 2015/0096; G01N 2015/1006; G01N 2015/1438; G01N 2021/4711; G01N 2021/556; G01N 2021/651; G01N 2021/8854; G01N 2021/887; G01N 21/27; G01N 21/35; G01N 21/3504; G01N 21/534; G01N 21/67; G01N 21/718; G01N 21/9505; G01N 21/9506; G01N 21/958; G01N 2201/103; G01N 2201/1045; G01N 2201/12; G01N 33/54326; G01N 33/54353; G02B 5/04; G02B 13/18; G02B 19/0028; G02B 19/0076; G02B 19/008; G02B 2003/0093; G02B 26/0808; G02B 3/04; G02B 5/001; G02B 21/0032; G02B 21/0056; G02B 27/58; G02B 5/0215; G02B 5/0236; G02B 5/0278; G02B 5/045; G02B 5/23; G01J 3/0216; G01J 3/0229; G01J 3/44; G01J 3/02; G01J 3/0218; G01J 3/36; G01J 3/427; G01J 2003/1213; G01J 2003/1217; G01J 3/10; G01J 3/32; G01J 3/4406

See application file for complete search history.

(56) References Cited

U.S. PATENT DOCUMENTS

| | | | |
|---|---|---|---|
| 6,606,157 B1* | 8/2003 | Kaye | G01N 15/1459 257/E31.039 |
| 2003/0223063 A1* | 12/2003 | Hill | G01N 15/0205 356/340 |
| 2006/0017926 A1* | 1/2006 | Pochy | G01N 15/0205 356/338 |
| 2007/0222987 A1* | 9/2007 | Palumbo | G01N 15/0227 356/338 |
| 2007/0285661 A1* | 12/2007 | Saunders | G01N 15/1459 356/336 |
| 2010/0035235 A1 | 2/2010 | Gabriel | |
| 2016/0252442 A1* | 9/2016 | Freitag | G01N 15/0211 356/336 |

FOREIGN PATENT DOCUMENTS

| | | |
|---|---|---|
| KR | 10-2012-0074558 | 7/2012 |
| KR | 10-1574435 | 12/2015 |

* cited by examiner

US 10,302,547 B2

PARTICLE SENSING DEVICE

CROSS-REFERENCE TO RELATED PATENT APPLICATIONS

This application is a U.S. National Stage Application under 35 U.S.C. § 371 of PCT Application No. PCT/KR2017/000072, filed Jan. 4, 2017, which claims priority to Korean Patent Application No. 10-2016-0001481, filed Jan. 6, 2016, whose entire disclosures are hereby incorporated by reference.

TECHNICAL FIELD

Embodiments relate to a particle sensing device.

BACKGROUND ART

There are various kinds of sensors used in touch panels of various electronic devices such as smart terminals, mobile phones, monitors, and TVs. Recently, various functions have been implemented using an optical sensor including a light emitter for emitting light and a light receiver for sensing light.

Hereinafter, a typical dust sensor will be described with reference to an accompanying drawing.

FIG. 1 is a cross-sectional view schematically showing a typical dust sensor 100.

The dust sensor 100 shown in FIG. 1 may consist of a light source 110, a lens 120, a mirror 122, a light receiver 130, and a light shield 140.

In the typical dust sensor 100 shown in FIG. 1, light emitted from the light source 110 is scattered by the dust 121 after passing through the lens 120. Then, the scattered light is incident on the light receiver 130. In this way, the typical dust sensor 100 checks various kinds of information such as the size, concentration, and amount of the dust 121 contained in the air using light. In the typical dust sensor 100, the light receiver 130 is disposed only on one side of the space where light is scattered. Specifically, the light receiver 130 is positioned in an area at 90° around the center of the space in which the dust 121 is sensed.

As shown in FIG. 1, according to a result of pre-conducted testing and simulation, when the light receiver 130 is disposed in an area at 90° around the center of the space where the dust is sensed, the intensity of the scattered light scattered by the dust 121 and incident on the light receiver 130 is not sufficiently high. Accordingly, the typical dust sensor 100 may not accurately receive the scattered light, and thus may not acquire correct information on the dust 121 due to low sensing sensitivity. Particularly, since the area of the light receiver 130 is very small, a cost for designing a separate circuit for amplifying the scattered light when an absorption amount of scattered light is insufficient may increase. Further, in the case of the typical dust sensor 100, the size of the dust sensor 100 may increase because the volume of the light receiver 130 is increased in order to increase sensing sensitivity.

DISCLOSURE

Technical Problem

Embodiments provide a particle sensing device which is capable of accurately acquiring information about particles because of excellent sensing sensitivity thereof, has a small volume, and may reduce manufacturing costs.

Technical Solution

In one embodiment, a particle sensing device may include a light emitter configured to emit and output light into a scattering space, and a light receiver disposed in a maximum scattering angle region where a maximum intensity of scattered light formed when the light emitted from the light emitter is scattered by a particle in the scattering space is obtained, the light receiver being configured to receive the scattered light incident thereon and generate a photocurrent signal.

For example, the light emitter may include a light source portion, and a light condenser disposed on an optical axis of the light source portion to condense light emitted from the light source portion.

For example, the maximum scattering angle region may include a first scattering region in a scattering angle range of 10° to 60°, for example, 15° to 45°, preferably, 20° to 30°, more preferably, 20° to 60°, with respect to an optical axis of the light emitter, and a second scattering region in a scattering angle range of −10° to −60°, for example, −15° to −45°, preferably, −20° to −30°, more preferably, −20° to −60°, with respect to the optical axis of the light emitter.

For example, the light receiver may include an opening allowing the light emitted from the light emitter and passed through the scattering space to be transmitted therethrough, a first light receiving region disposed in the first scattering region of the maximum scattering angle region in a periphery of the opening, and a second light receiving region disposed in the second scattering region of the maximum scattering angle region in the periphery of the opening.

For example, the first and second light receiving regions may be disposed on an upper side and a lower side of the opening, respectively, in a direction intersecting the optical axis.

For example, the first and second light receiving regions may be integrated with each other.

For example, a width of the opening is greater than a width of the first and second light receiving regions in a direction intersecting the optical axis. In this case, the first and second light receiving regions may be separated from each other in a direction intersecting the optical axis.

For example, the light receiver may have a concave cross-sectional shape having a constant curvature.

For example, the particle sensing device may further include a substrate having the light receiver disposed thereon. For example, the light receiver may include an organic thin film photodiode. For example, the organic thin film photodiode may include a first electrode disposed on the substrate, an activation layer disposed on the first electrode, and a second electrode including at least one of a first sub-electrode or a second sub-electrode, wherein the first sub-electrode may be disposed on the substrate, and the second sub-electrode may be disposed on the activation layer and is connected to the first sub-electrode. For example, the organic thin film photodiode may further include a buffer layer disposed between the first electrode and the activation layer, and a protective layer disposed on the second sub-electrode.

For example, the particle sensing device may further include a controller configured to analyze information on the particle using the photocurrent signal generated by the light receiver, and a wire arranged to transmit the photocurrent signal generated by the light receiver to the controller.

For example, the particle sensing device may further include a printed circuit board having the controller disposed thereon.

For example, the light receiver and the wire may be disposed on the substrate, wherein the substrate may include a pliable substrate, wherein the first and second light receiving regions may be disposed around the opening on the pliable substrate to define the opening.

For example, a portion of the pliable substrate corresponding to the opening may be light-transmissive. Alternatively, a portion of the pliable substrate corresponding to the opening may have a shape of a through hole.

For example, the particle sensing device may further include an optical trap portion configured to trap light having passed through the through hole corresponding to the opening of the light receiver.

For example, the particle sensing device may further include a housing configured to accommodate the light emitter and the light receiver and to form the scattering space.

Advantageous Effects

According to embodiments, a particle sensing device may increase the sensing sensitivity of a particle with a light receiver arranged in a maximum scattering angle range where the intensity of the scattered light is maximized, and may further increase the sensing sensitivity in sensing the scattered light with first and second light receiving regions symmetrically arranged on upper and lower sides of an optical axis of a light emitter. Further, the particle sensing device may reduce the cost for designing a circuit for amplifying a signal as it may not require or may simplify a separate circuit for amplifying signals due to low reception intensity of scattered light. When the light receiver is implemented in the form of a thin film on the substrate, the thickness of the whole electronic device including the particle sensing device may be reduced and thus become lightweight.

Since an organic thin film photodiode, which is formed on a transparent substrate, is used as the light receiver, the light receiver may be designed without restriction as to the area and shape thereof. In addition, compared to a conventional case where a photodiode module is mounted on a silicon wafer, organic thin film photodiodes may be fabricated at once through a printing process, and accordingly the manufacturing time and processes may be shortened. Further, since no separate light condenser is required on the side of the light receiver to condense scattered light, manufacturing costs may be further reduced and a compact design may be realized.

BEST MODE

Hereinafter, embodiments will be described in detail to facilitate understanding of the technical spirit of the present disclosure and are not intended to limit the present disclosure. In addition, the details illustrated in the accompanying drawings are provided to easily describe embodiments of the present disclosure and may be different from the forms actually taken in the implementation thereof.

It should also be noted that each constituent described below is only an example for implementing the present disclosure. Thus, in other implementations of the disclosure, other constituents may be employed without departing from the spirit and scope of the disclosure.

In addition, the expression "comprising" is an open-ended phrase merely indicating presence of elements and should not be understood as excluding any additional elements.

In addition, expressions such as "first" and "second" are used only for the purpose of distinguishing a plurality of elements from each other, and do not limit the order or other features of the elements.

In the description of embodiments, it is to be understood that when a layer (film), region, pattern or structure is described as being "on" or "under" a substrate, a layer (film), a region, a pad, or a pattern, the terms "on" and "under" conceptually include "directly" or "with another layer interposed therebetween". In the description, "on" or "under" is defined based on the drawings.

When it is stated that one part is "connected" to another, it should be understood that this includes not only a case where one part is "directly connected" to another but also a case where the parts are indirectly connected to each other with another member placed therebetween. In addition, when it is stated that a part "includes" an element, this means that the part may further have other elements rather than excluding the other elements, unless specifically stated otherwise.

Hereinafter, particle sensing devices 200A, 200B, and 200C according to embodiments will be described with reference to the accompanying drawings. For simplicity, the particle sensing devices 200A, 200B, and 200C will be described using the Cartesian coordinate system (x axis, y axis, and z axis), but it is to be noted that other coordinate systems may also be employed to describe the devices.

Figure 1:
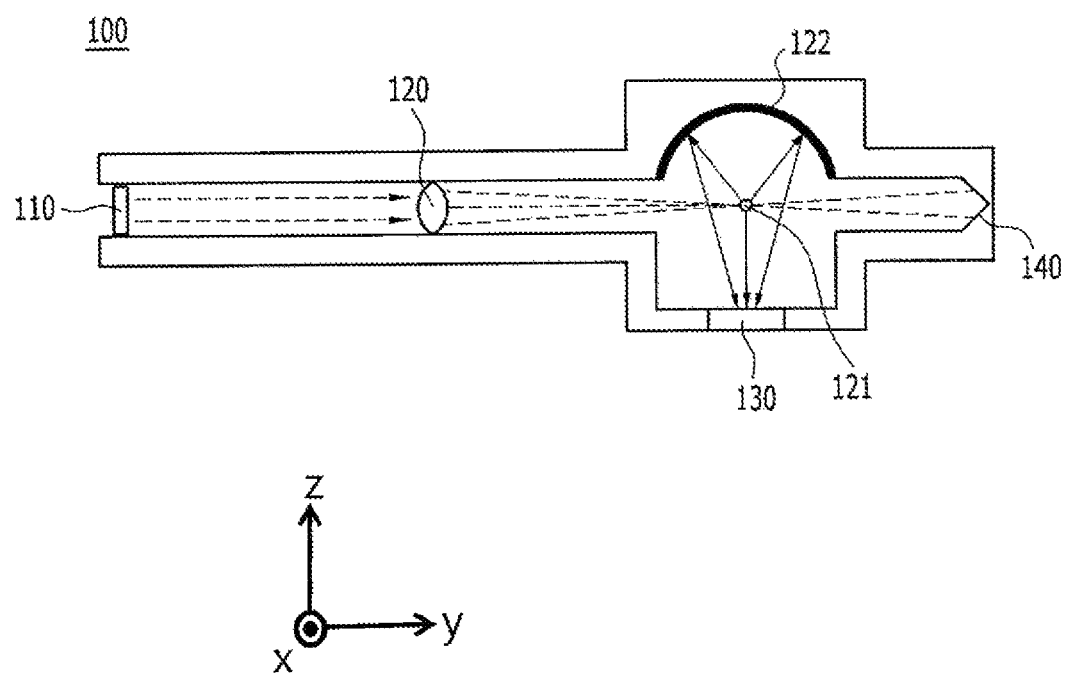
FIG. 1 is a cross-sectional view schematically showing a typical dust sensor.
Figure 2:
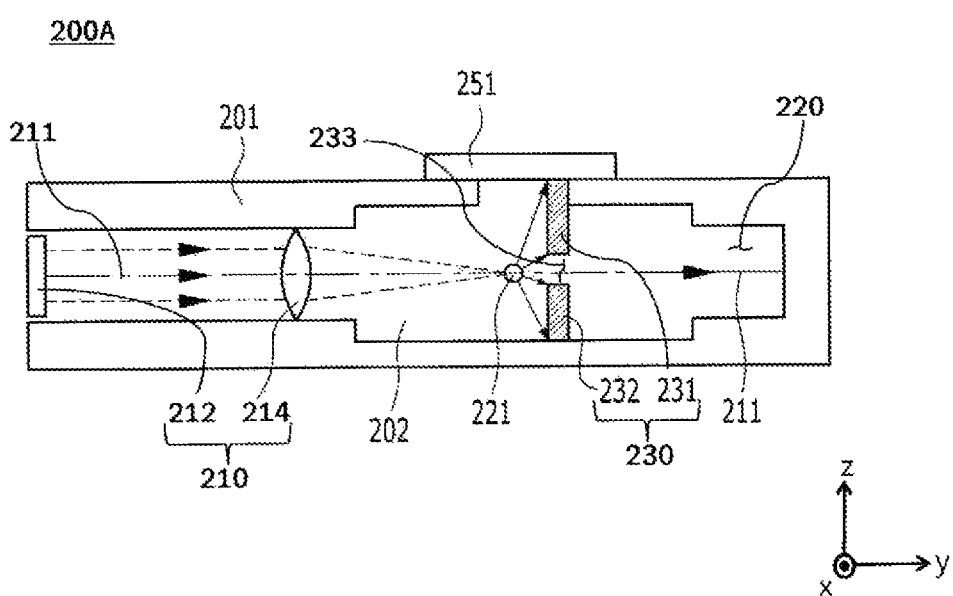
FIG. 2 is a cross-sectional view schematically showing a particle sensing device according to an embodiment.

FIG. 2 is a cross-sectional view schematically showing a particle sensing device 200A according to an embodiment.

The particle sensing device 200A shown in FIG. 2 may include a housing 201, a light emitter 210, an optical trap portion 220, a light receiver 230, a printed circuit board 251, and a controller (not shown).

The light emitter 210 serves to emit light (or generate an optical signal) and output (or radiate) the light into a scattering space 202. The housing 201 serves to accommodate the light emitter 210 and the light receiver 230, and corresponds to an optical chamber. For example, the scattering space 202 may be formed by the housing 201 as illustrated in FIG. 2. Here, the scattering space 202 may be defined as a space where light is scattered by a particle 221.

Here, the particle 221 may be dust or smoke floating in the air, and embodiments are not limited to a specific type of the particle 221.

The light emitter 210 may include a light source portion 212 and a light condenser 214.

Basically, the light source portion 212 may omnidirectionally radiate light. In particular, the light source portion 212 may radiate light along an optical path formed in a direction (for example, the y-axis direction) pointing toward the light condenser 214. The light radiated from the light emitter 210 to the scattering space 202 may be scattered by the particle 221 introduced into the particle sensing device 200A.

For example, the light source portion 212 may include at least one of a light emitting diode (LED), an organic light emitting diode (OLED), an infrared light emitting diode, or a laser diode, but embodiments are not limited thereto.

In addition, the light source portion 212 may be supplied with power from an electronic device (not shown), which may be included in or include the particle sensing device 200A, and emit the supplied energy in the form of light having a specific wavelength. Further, the light source portion 212 may use various materials to change the wavelength of the radiated light as needed.

The light condenser 214 is disposed on the optical path along which the light emitted from the light source portion 212 travels, thereby serving to condense light radiated by the light source portion 212. That is, the light condenser 214 may be disposed on an optical axis 211 of the light emitter 210 (or the light source portion 212).

The light condenser 214 may be implemented in various forms to condense the light emitted from the light source portion 212. For example, the light condenser 214 may include at least one of a convex lens, a plano-convex lens, a concave lens, or a concave mirror, but embodiments are not limited thereto. Various other commonly-used light-condensing elements may be applied to realize the light condenser 214.

Next, after light emitted from the light source portion 212 is condensed by the light condenser 214 and is radiated into the scattering space 202, the scattered light formed when the light is scattered by the particle 221 may be incident on (or received by) the light receiver 230 with the path thereof changed. Then, the light receiver 230 may generate a photocurrent signal using the incident scattered light. The light receiver 230 may be formed on the optical axis 211 to receive the scattered light more accurately. More preferably, an opening 233 of the light receiver 230 may be formed on the optical axis 211 to allow rays which are not scattered among the rays of light condensed by the light condenser 214 to be transmitted therethrough, such that the scattered light may be received more accurately.

According to an embodiment, the light receiver 230 may be disposed in a "maximum scattering angle region". Here, the "maximum scattering angle region" may refer to a region where the intensity of light (hereinafter referred to as "scattered light") formed when the light emitted from the light emitter 210 is scattered by the particle 221 in the scattering space 202 is maximized.

Figure 3A:
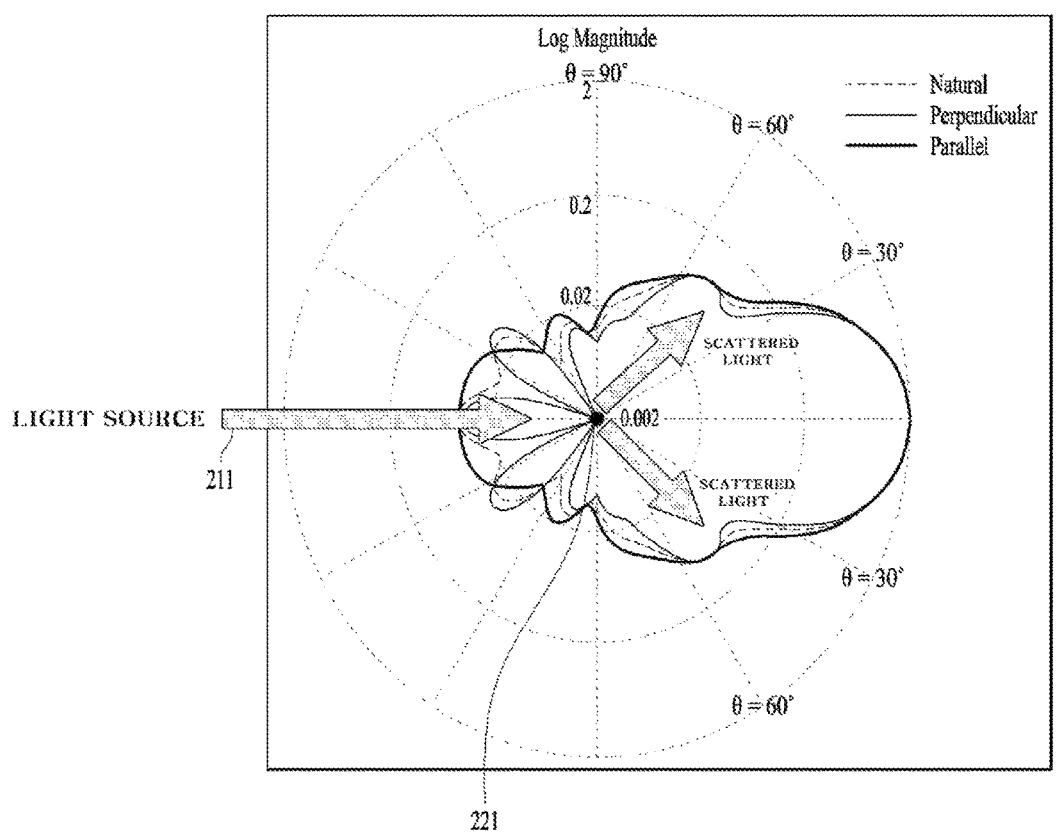
FIGS. 3A to 3C illustrate a maximum scattering angle region.
Figure 3B:
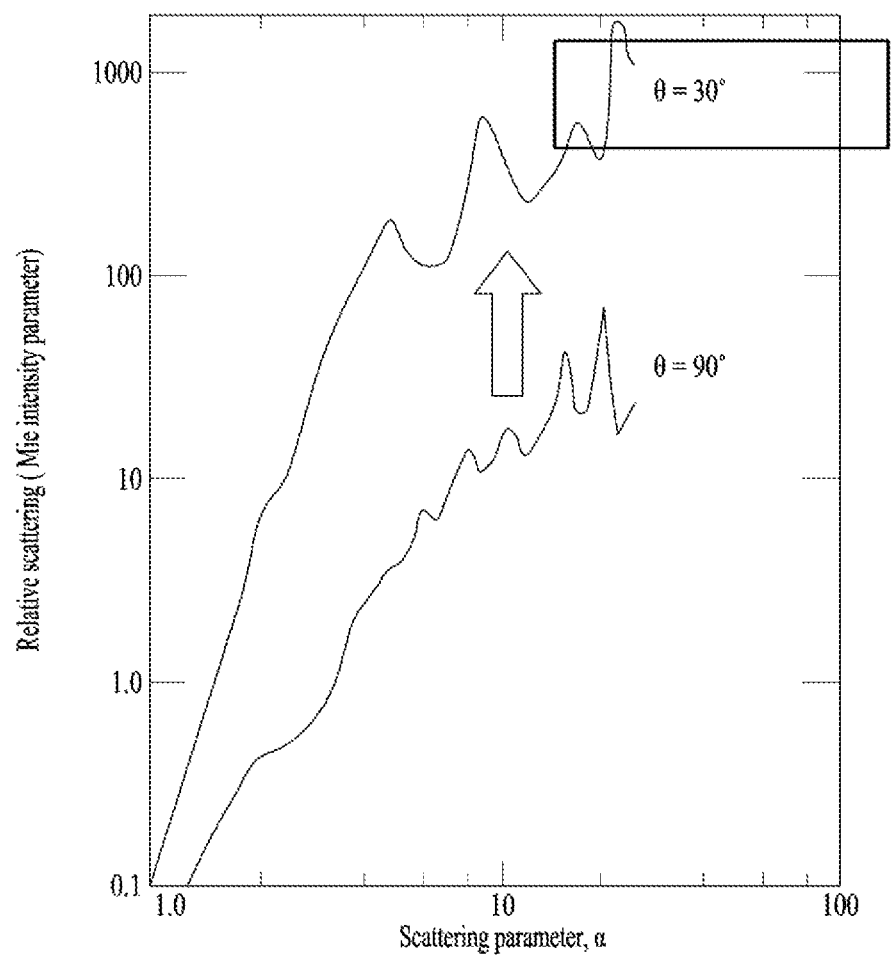
Figure 3C:
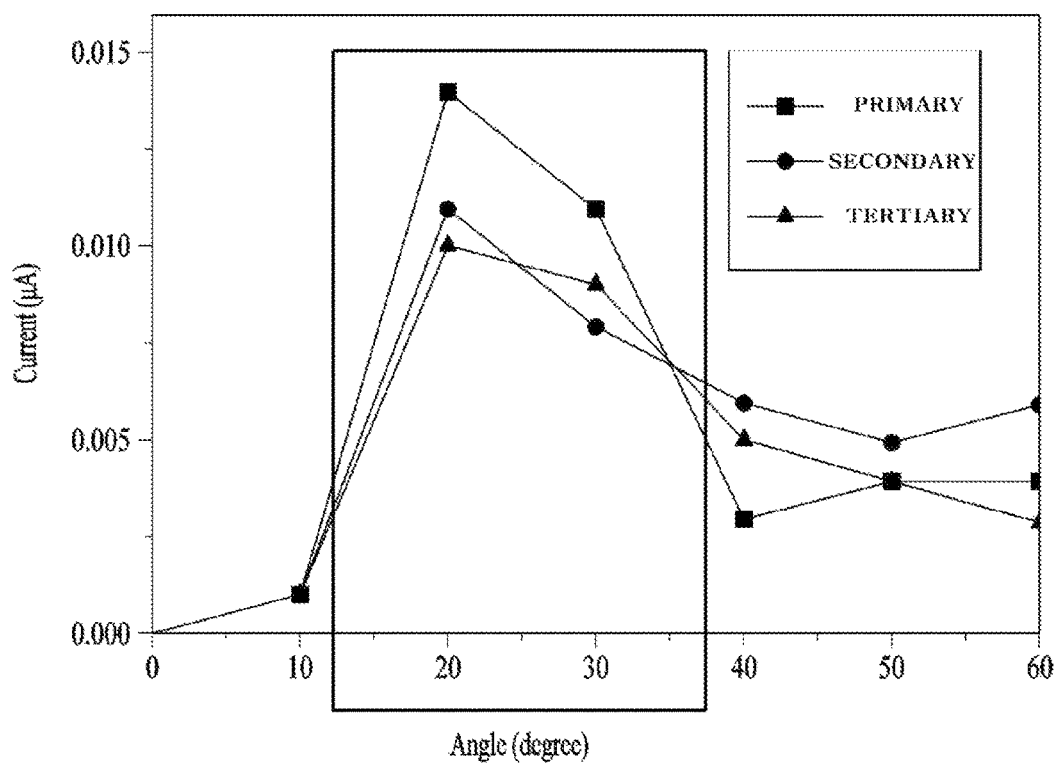

FIGS. 3A to 3C illustrate a maximum scattering angle region.

FIG. 3A shows the angle θ of scattered light formed when the light emitted from the light source (portion) 212 is scattered by the particle 221 on the optical axis 211. FIG. 3B is a graph depicting the intensity of light per each scattering angle θ, where the horizontal axis corresponds to a scattering parameter and the vertical axis corresponds to relative scattering. FIG. 3C is a graph depicting variation of a photocurrent signal according to the scattering angle θ, wherein the horizontal axis corresponds to the scattering angle θ and the vertical axis corresponds to the photocurrent signal.

Referring to FIG. 3A, it can be seen that the intensity of the scattered light is not high at a point (θ=90°) turned by 90° with respect to the travel direction (i.e., the direction of the optical axis) of the light emitted from the light source (portion) 212. Rather, it can be seen that the intensity of the scattered light is maximized at the scattering angle θ in a region of the angular range of 20° to 60° with respect to the optical axis 211.

Figure 4:
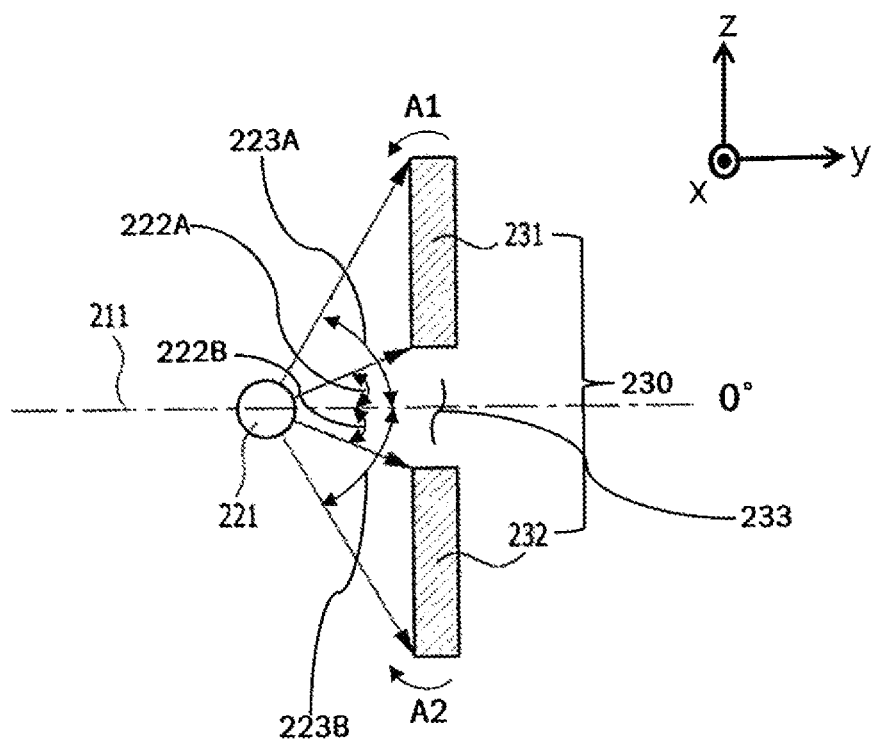
FIG. 4 is an enlarged cross-sectional view of the light receiver shown in FIG. 2.

FIG. 4 is an enlarged cross-sectional view of the light receiver 230 shown in FIG. 2.

Referring to FIG. 4, the scattering angle θ may refer to angles 222A, 222B, 223A and 223B at which light is scattered by the particle 221 when a point at which the light condensed by the light condenser 214 meets the particle 221 on the optical axis 211 is taken as a vertex and the optical path of the light is taken as a central axis (i.e., optical axis) 211. The positions of the particle 221 may be scattered in particle sensing device 200A. Accordingly, the scattering angle may be measured by taking a point at which the light condensed by the light condenser 214 meets the particle 221 positioned at the point on the extension of the central axis (or optical axis) 211 of the optical path as a vertex. The vertex may be the center point of the sensing space 202.

In addition, referring to FIG. 3B, change in the intensity of the scattered light according to the scattering angle θ can be seen. It can be seen that the intensity (or strength) of the scattered light at the scattering angle θ of 30° is about 10 times that at the scattering angle θ of 90°.

More specifically, it can be seen from experimentation that the strength of the photocurrent signal generated by the light receiver 230 varies depending on the scattering angle θ, as shown in the graph of FIG. 3C. Referring to FIG. 3C, it can be seen that, when the scattering angle θ rapidly changes from 10° to 20°, the strength of the photocurrent signal increases sharply. Therefore, the light receiver 230 may be disposed in the maximum scattering angle region where the intensity of the scattered light may be maximized, such that the intensity of the photocurrent may be maximized.

According to an embodiment, the maximum scattering angle region may include first and second scattering regions.

Referring to FIG. 4, the first scattering region may be a region within a scattering angle range of 10° to 60°, for example, 15° to 45°, preferably, 20° to 30°, more preferably, 20° to 60°, with respect to the optical axis 211 of the light emitter 210. Hereinafter, a region belonging to a range having the scattering angle 222A of 20° and the scattering angle 223A of 60° will be described as corresponding to the first scattering region, but embodiments are not limited thereto.

The second scattering region may be a region within a scattering angle range of −10° to −60°, for example, −15° to −45°, preferably, −20° to −30°, more preferably, −20° to −60°, with respect to the optical axis 211 of the light emitter 210. Hereinafter, a region belonging to a range having the scattering angle 222A of −20° and the scattering angle 223B of −60° will be described as corresponding to the second scattering region, but embodiments are not limited thereto.

The light receiver 230 may include an opening 233 and first and second light receiving regions 231 and 232.

The opening 233 may be a portion of the light receiver 230 that allows light emitted from the light emitter 210 and passing through the scattering space 202 to be transmitted therethrough. The first light receiving region 231 may be disposed in the first scattering region of the maximum scattering angle region in the periphery of the opening 233. The second light receiving region 232 may be disposed in the second scattering region of the maximum scattering angle region in the periphery of the opening 233.

The first and second light receiving regions 231 and 232 may symmetrically be arranged in a direction perpendicular to the optical axis 211 (for example, the z-axis direction), but embodiments are not limited thereto. The scattered light formed by being scattered by the particle 221 may be scattered in several directions. In this case, arranging the first and second light receiving regions 231 and 232 in the first and second scattering regions, respectively, in the z-axis direction perpendicular to the optical path 211 may maximize the intensity of the scattered light received by the light receiver 230. That is, each of the first and second light receiving regions 231 and 232 is a region for receiving light scattered by the particle 221, and arranging the light receiving regions in the first and second scattering regions respectively may increase the intensity of the photocurrent.

Further, the first and second light receiving regions 231 and 232 may be formed in a planar shape.

In the case of FIG. 2, the first and second light receiving regions 231 and 232 are illustrated as being arranged straight in the z-axis direction. That is, the light receiver 230 may be arranged such that the direction perpendicular to the surface of the light receiver 230 is parallel to the optical axis 211, which is the central axis of the optical path. However, embodiments are not limited thereto.

That is, according to another embodiment, the first and second light receiving regions 231 and 232 may be disposed in the first and second scattering regions, respectively, so as to be inclined at a certain angle advantageous for receiving light scattered by the particle 221. For example, the first and second light receiving regions 231 and 232 may be arranged to be inclined in the directions A1 and A2 indicated by the arrows shown in FIG. 4. That is, the light receiver 230 may be inclined such that the direction perpendicular to the surface of the light receiver 230 forms a certain acute angle with respect to the optical axis 211, which is the central axis of the optical path.

Although FIG. 2 illustrates that the first and second light receiving regions 231 and 232 of the light receiver 230 are arranged in the direction (for example, the z-axis direction) perpendicular to the optical axis 211, embodiments are not limited thereto. In order to adjust the scattering angle and the scattering distance, a portion of the light receiver 230 spaced farther from the particle 221 may be brought to a position closer to the particle 221 such that the angle formed between the cross section of the light receiver 230 and the optical axis 211 may be between 0° and 90°.

Figure 5:
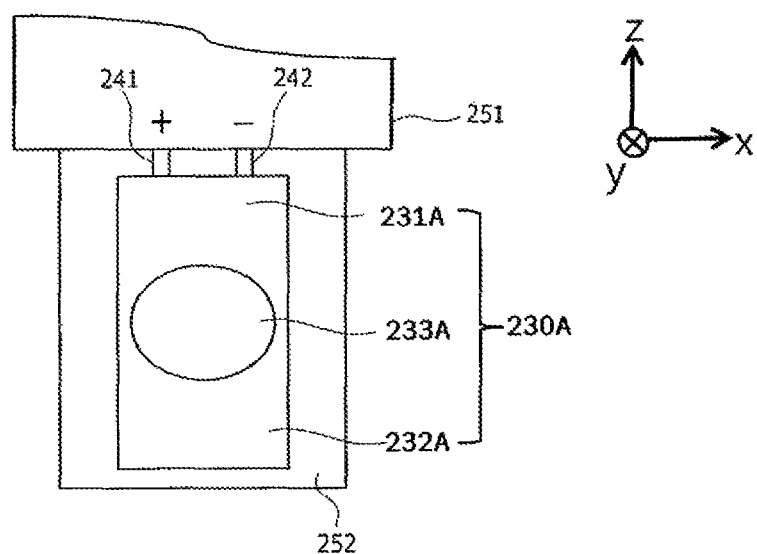
FIG. 5 is a left side view illustrating an embodiment of the light receiver shown in FIG. 2.
Figure 6:
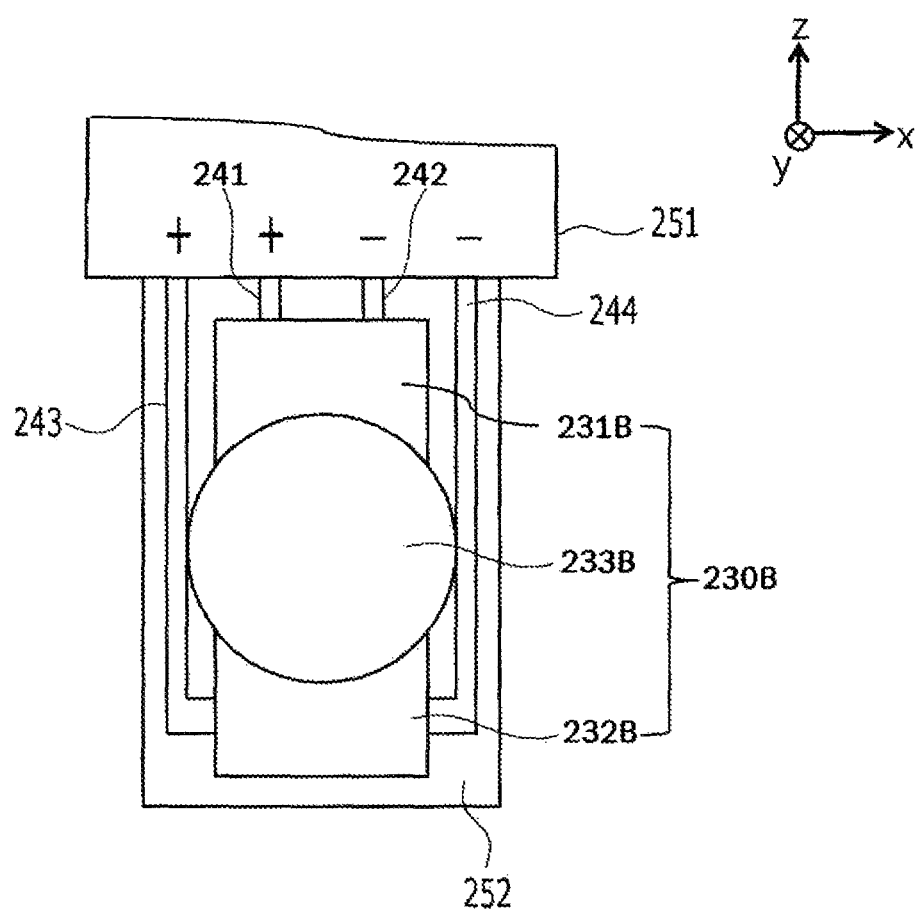
FIG. 6 is a left side view illustrating another embodiment of the light receiver shown in FIG. 2.

FIG. 5 is a left side view illustrating an embodiment 230A of the light receiver 230 shown in FIG. 2, and FIG. 6 is a left side view illustrating another embodiment 230B of the light receiver 230 shown in FIG. 2. Here, "231A" and "231B" correspond to embodiments of the first light receiving region 231 shown in FIG. 2, "232A" and "232B" correspond to embodiments of the second light receiving region 232 shown in FIG. 2, and "233A" and "233B" correspond to embodiments of the opening 233 shown in FIG. 2.

Referring to FIGS. 2, 5 and 6, the opening 233A, 233B may be formed at a point on the extension of the central axis of the optical path of the light condensed by the light condenser 214 and have a certain size. That is, the opening 233A, 233B may be formed at a point of the light receiver 230A, 230B which meets the optical axis 211. The first light receiving region 231A, 231B may be arranged over (i.e., on the upper side of) the opening 233A, 233B, and the second light receiving region 232A, 232B may be arranged under (i.e., on the lower side of) the opening 233A, 233B, in a direction (for example, the z-axis direction) intersecting the optical axis 211.

The first light receiving region 231A, 231B arranged over the opening 233A, 233B may receive an upper portion of the scattered light formed according to scattering by the particle 221, and the second light receiving region 232A, 232B arranged under the opening 233A, 233B may receive a lower portion of the scattered light formed according to scattering by the particle 221.

When a light receiving region is formed on only one of the upper and lower sides of the opening 233A, 233B, the sensed intensity of the scattered light may be low. On the other hand, as shown in FIGS. 2, 4, 5 and 6, when the opening 233 (233A, 233B) is disposed in the light receiver 230 (230A, 230B), the first light receiving region 231A, 231B is arranged over the opening 233 (233A, 233B), and the second light receiving region 232A, 232B is arranged under the opening 233 (233A, 233B), namely, the light receiving regions 231 and 232 are arranged on both the upper side and the lower side of the opening 233A, 233B, the amount of the scattered light received may be maximized, and thus the sensing sensitivity may be further improved.

In an embodiment, as shown in FIG. 5, the first light receiving region 231A and the second light receiving region 232A may be integrally connected to each other.

Alternatively, as shown in FIG. 6, the first light receiving region 231B and the second light receiving region 232B may be separated and isolated by the opening 233B in a direction (for example, the z-axis direction) intersecting the optical axis 211. Since the width of the opening 233B is greater than the width of the first and second light receiving regions 231B and 232B in the direction (for example, the x-axis direction) intersecting the optical axis 211, the first light receiving region 231B and the second light receiving region 232B may be separated from each other by the opening 233B.

As described above, the first light receiving region 231A, 231B is disposed in the first scattering region having a scattering angle range of 20° to 60° with respect to the optical axis 211, and the second light receiving region 232A, 232B is disposed in the second scattering region having a scattering angle range of −20° to −60° with respect to the optical axis 211. Thereby, the scattered light incident in the range of the scattering angle θ of 0° to 20° and 0° to −20° may be transmitted through the opening 233A, 233B.

The controller (not shown) may obtain information on the particles (for example, information on at least one of the size, concentration or quantity of the particles) by analyzing the photocurrent signal generated by the light receiver 230 (230A, 230B). In this operation, the controller may analyze the photocurrent signal according to predetermined conditions. In addition, the controller may appropriately analyze the photocurrent signal according to the purpose and usage of an electronic device including the sensor. The controller may be implemented in the form of an application specific integrated circuit (ASIC) provided on a substrate 252.

The particle sensing device 200A may further include a wire for transmitting the photocurrent signal generated by the light receiver 230 (230A, 230B) to the controller.

The light receiver 230 may be divided into a plurality of light receiving regions 231 and 232 by the opening 233. Therefore, the light receiver 230 may efficiently increase the light reception efficiency even if a plurality of light receivers 230 each requiring a wire is not arranged in the first and second scattering regions, respectively.

In addition, the light receiver 230A shown in FIG. 5 may transmit the photocurrent signal to the controller through one pair of wires 241 and 242 alone because the first light receiving region 231A on the upper side and the second light receiving region 232A on the lower side are integrally connected to each other. By contrast, the light receiver 230B shown in FIG. 6 may transmit the photocurrent signal to the controller through two pairs of wires 241, 242, 243, and 244 respectively connected to the first and second light receiving regions 231B and 232B because the first light receiving region 231B and the second light receiving region 232B are separated from each other by the opening 233B.

If the first and second light receiving regions 231B and 232B are separated by increasing the area of the opening 233B as shown in FIG. 6, photocurrent signals (or sensing signals) may be separately received from each of the light receiving regions 231B and 232B, and therefore the particle sensing device 200A may more accurately identify the position where the particle 221 is sensed. This is because the light receiver 230B of FIG. 6 allows a photocurrent signal to be transmitted to the controller through some wires 241 and 242 when the scattered light is incident on the first light receiving region 231B and allows a photocurrent signal to be transmitted to the controller through the other wires 243 and 244 when the scattered light is incident on the second light receiving region 232B, while the light receiver 230A of FIG. 5 causes a photocurrent signal to be transmitted to the controller through the same wires 241 and 242 regardless of whether the scattered light is incident on the first light receiving region 231A or the second light receiving region 232A.

The wires 241, 242, 243, and 244 shown in FIGS. 5 and 6 may be implemented using conductive wires for contacting respective components to each other to form a circuit or a line, and may be implemented using any conductors which are commonly used.

Referring to FIGS. 5 and 6, the wires may include a positive (+) wire 241, 243 and a negative (−) wire 242, 244, which connect the light receiver 230A, 230B and the controller. The light receiver 230A, 230B may include a first electrode and a second electrode. The first electrode may be configured to transmit/receive a positive (+) signal, and the second electrode may be configured to transmit/receive a negative (−) signal. Therefore, the light receiver 230A, 230B may transmit a positive (+) photocurrent signal to the controller through the positive (+) wire 241, 243, and transmit a negative (−) photocurrent signal to the controller through the negative (−) wire 242, 244.

In addition, the particle sensing device 200A according to an embodiment may further include a substrate 252. According to the embodiments, as illustrated in FIGS. 5 and 6, the light receiver 230A, 230B and the wires 241, 242, 243, 244 may all be disposed on the substrate 252.

The light receiver 230A, 230B may be disposed in close contact with the substrate 252 (for example, a pliable substrate). According to one embodiment, the light receiver 230A, 230B may be disposed in the form of a thin film in close contact with the upper surface or lower surface of the substrate 252. For example, the light receiver 230A, 230B may be disposed on the upper surface of the substrate 252 by sintering a paste material through plastic processing. Alternatively, the light receiver 230A, 230B may be formed in close contact with the upper surface of the substrate 252 (for example, a pliable substrate) using at least one of a vacuum deposition method, a CVD method, or a printing method. When a very thin film is formed on the substrate 252 (for example, a pliable substrate) using vacuum deposition, patterning, or the like, there is an advantage that the electronic device including the particle sensing device 200A may become thin and light.

The first light receiving region 231A, 231B and the second light receiving region 232A, 232B may be disposed around the opening 233A, 233B on the substrate 252 to define the opening 233A, 233B.

Here, the substrate 252 may be a pliable substrate. The pliable substrate 252 may have a curved shape. The first light receiving region 231A, 231B, the second light receiving region 232A, 232B and the wires 241, 242, 243, 244 may be disposed on a typical substrate. Alternatively, in order to realize an integrated light receiving module, the first light receiving region 231A, 231B, the second light receiving region 232A, 232B and the wires 241, 242, 243, 244 may be disposed on a pliable substrate 252 capable of implementing a bending property.

Further, the pliable substrate 252 may be a flexible substrate having flexibility. In an embodiment, the pliable substrate 252 may be a curved or bended substrate. For example, the pliable substrate 252 may include glass or plastic. Specifically, the pliable substrate 252 may include chemically reinforced/semi-tempered glass such as soda lime glass or aluminosilicate glass, may include reinforced or soft plastic such as polyimide (PI), polyethylene terephthalate (PET), propylene glycol (PPG), or polycarbonate (PC), or may include sapphire.

Further, the pliable substrate 252 may include an optically isotropic film. For example, the pliable substrate 252 may include cyclic olefin copolymer (COC), cyclic olefin polymer (COP), optically isotropic polycarbonate (PC), or optically isotropic polymethylmethacrylate (PMMA).

Further, the substrate 252 may be bent to partially have a curved surface. That is, the substrate 252 may be bent in a manner that it partially has a flat surface and partially has a curved surface. Specifically, an end of the transparent substrate 252 may be bent to have a curved surface or may be bent or curved to have a surface including a random curvature. In an embodiment, the pliable substrate 252 may be configured as a flexible substrate having a double-curved surface.

In addition, the particle sensing device 200A may further include a printed circuit board 251, on which the controller is disposed. The printed circuit board 251 may extend from the substrate 252 or may be formed on the substrate 252 as another layer. The printed circuit board 251, which is formed to be electrically conductive by drawing a circuit on a board in connecting the components of an electronic product with the circuit, is widely used in typical electronic products.

In addition, a part of the pliable substrate 252 corresponding to the opening 233A, 233B may be light-transmissive. That is, the first light receiving region 231A, 231B and the second light receiving region 232A, 232B which have a shape as shown in FIGS. 5 and 6 may be formed on portions of the pliable substrate 252 of a transparent material except the opening 233A, 233B to define the opening 233A, 233B having light transmittability.

Alternatively, a portion of the pliable substrate 252 corresponding to the opening 233A, 233B may have a through-hole shape. That is, a hole may be actually cut in the substrate 252 to form the opening 233A, 233B.

Figure 7:
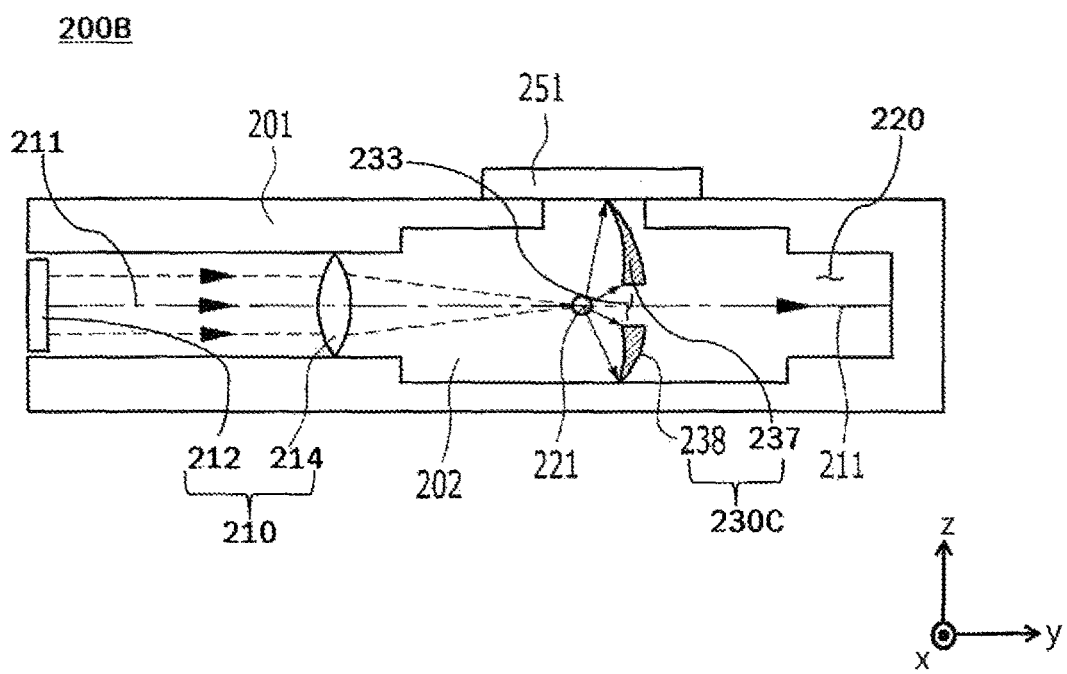
FIG. 7 is a cross-sectional view schematically showing a particle sensing device according to another embodiment.

FIG. 7 is a cross-sectional view schematically showing a particle sensing device 200B according to another embodiment.

Referring to FIG. 7, the particle sensing device 200B according to another embodiment may include a housing 201, a light emitter 210, an optical trap portion 220, a light receiver 230C, a printed circuit board 251, and a controller. Here, in the particle sensing device 200B shown in FIG. 7, the same parts as those of the particle sensing device 200A shown in FIG. 2 are assigned the same reference numerals, and redundant description thereof will be omitted. Therefore, the description of the particle sensing device 200A shown in FIG. 2 may be applied to the particle sensing device 200B shown in FIG. 7, unless specifically stated otherwise.

Unlike the light receiver 230 shown in FIG. 2, the light receiver according to another embodiment may have a constant curvature. For example, the light receiver 230C may have a concave cross-sectional shape having a constant curvature, as illustrated in FIG. 7. The particle sensing device 200B shown in FIG. 7 is the same as the particle sensing device 200A shown in FIG. 2, except that the light receiver 230C has a different shape from the light receiver 230 shown in FIG. 2.

In the case where the substrate 252 is a pliable substrate as described above, the pliable substrate may be implemented in a curved shape, and the light receiver 230C formed on the pliable substrate may also be implemented in a curved shape having a curvature. In this case, the curvature of the light receiver 230C may be in a range of 0.5 R to 10 R, but embodiments are not limited thereto. In addition, the distance from the center of the scattering space 202 (for example, the point at which the particle 221 is positioned) to the light receiver 230C may be 0.5 mm to 10 mm, but embodiments are not limited thereto.

To implement the light receiver 230C having a curvature, the pliable substrate 252 may include at least one of a U-shape, a square bracket shape, a trapezoidal shape, a triangular shape, or a V-shape, but embodiments are not limited thereto. However, in the case where the pliable substrate 252 is implemented in an angled shape, there is a possibility that the light receiver 230C or the wires disposed on the pliable substrate 252 will be damaged. Therefore, the light receiver 230C and the wires may all be implemented using flexible elements and the pliable substrate 252 may be bent in a U-shape.

Through shape deformation (bending) of the substrate 252 and the light receiver 230C, the particle sensing device may include a flat or curved light receiver 230C. Particularly, with the curved light receiver 230C, an improvement may be obtained regarding variation in sensing sensitivity per positions of the particle 221. As the scattering angle θ increases, the distance between the particle 221 and the light receiver increases. When the light receiver 230C is formed to be concave as shown in FIG. 7, the distances of the light scattered by the particle 221 to the light receiver 230C may be corrected so as to be similar to each other. Accordingly, decrease in the intensity of the scattered light according to increase in the scattering angle θ may be addressed.

As the light receiver 230 (230A, 230B) is disposed at a portion of the particle sensing device 200A, 200B according to the above-described embodiments where the intensity of the scattered light is maximized, the intensity of the received scattered light is high. Accordingly, a separate part for amplifying the signal according to reception of weakly scattered light may be omitted or simplified, and cost for designing a circuit for amplifying the signal may be reduced.

Next, the optical trap portion 220 of the particle sensing devices 200A and 200B shown in FIGS. 2 and 7 is formed on the optical axis 211 and serves to trap the light passed through the opening 233 of the light receiver 230. For example, when a hole is cut in the substrate 220 to form a through hole, or the first light receiving region 231A, 231B and the second light receiving region 232A, 232B are formed on portions of the pliable substrate 252 of a transparent material except the opening 233A, 233B, light passed through the through hole or the opening 233A, 233B on the pliable substrate 252 of the transparent material may travel up to the optical trap portion 220.

Referring back to FIGS. 2 and 7, the light receiver 230, 230C may be implemented using at least one of a photodiode, a photomultiplier, or a phototransistor. In particular, the light receiver 230, 230C may be implemented using an organic thin film photodiode. When the light receiver 230, 230C is implemented using an organic thin film photodiode, the structure of the light receiver 230, 230C may be designed without restriction as to the area and shape thereof.

The organic thin film photodiode is an organic material-based element that may replace the photodetector. The organic thin film photodiode may improve light sensitivity of electronic devices such as cameras and may be used to examine whether a display can be implemented with uniform color composition.

In addition, compared to inorganic materials, there is an advantage that the organic thin film photodiode is very light and less expensive to produce, and is usable in flexible applications.

Since organic materials may be sensitive only to a specific wavelength band (e.g., red light, green light, blue light, etc.) depending on the substances thereof, the spectral sensitivity of the optical sensor may be adjusted by selecting an appropriate material according to application. In addition, the organic materials have many advantages such as a good absorption spectrum from UV to IR, a high photogeneration yield, and an ability to accommodate almost all substrate processes through a relatively low-temperature processing capability compared to inorganic materials.

Hereinafter, an organic thin film photodiode for embodying the light receiver 230, 230C of the particle sensing device 200A, 200B according to the embodiments will be described with reference to the accompanying drawings.

Figure 8:
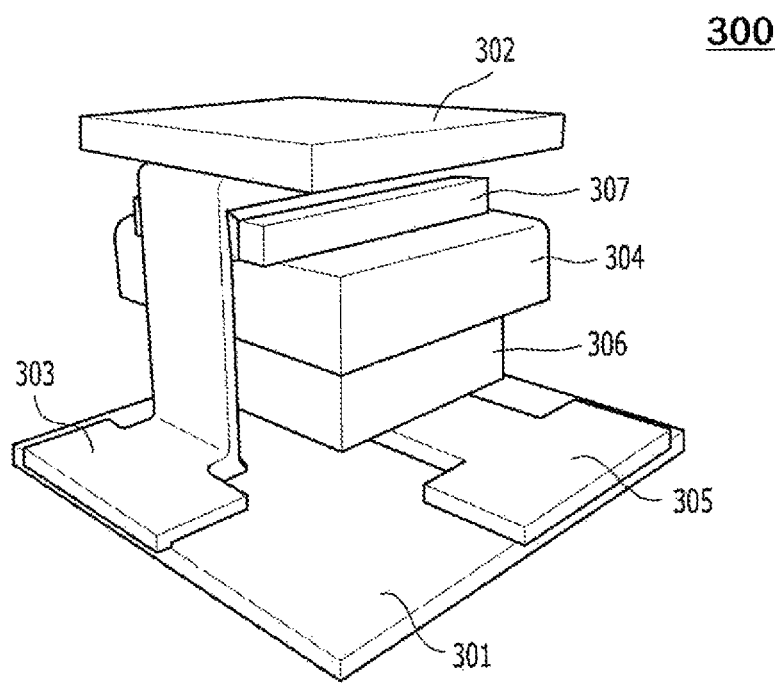
FIGS. 8 and 9 are external perspective views schematically showing an organic thin film photodiode according to an embodiment.
Figure 9:
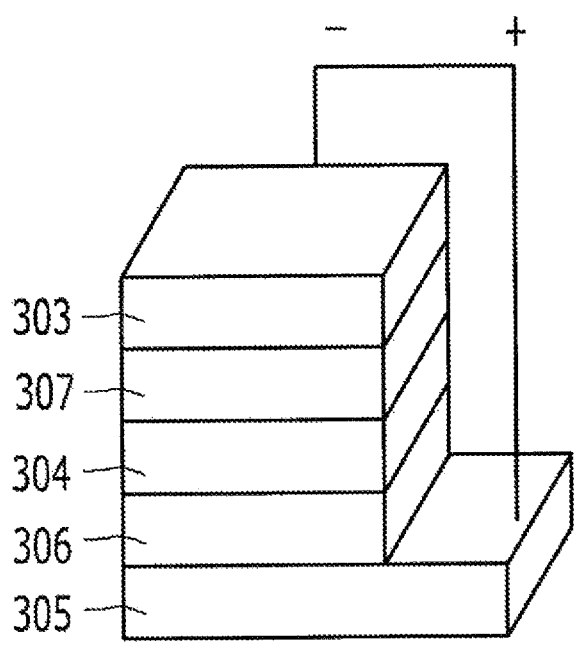

FIGS. 8 and 9 are external perspective views schematically showing an organic thin film photodiode 300 according to an embodiment.

The organic thin film photodiode 300 shown in FIGS. 8 and 9 may include a first electrode 305, an activation layer 304, and a second electrode 303, 307. The light receivers 230, 230A, 230B, and 230C shown in FIGS. 2, 5, 6, and 7 may be implemented as illustrated in FIGS. 8 and 9, but embodiments are not limited thereto.

Referring to FIG. 8, the first electrode 305, the activation layer 304, and the second electrode 303, 307 may be stacked on a substrate 301.

The organic thin film photodiode 300 may be laminated on the pliable substrate 252, but embodiments are not limited thereto. According to another embodiment, a separate substrate may be disposed on the pliable substrate 252, and the organic thin film photodiode 300 may be disposed on the separate substrate. Thus, the substrate 301 shown in FIG. 8 may correspond to the substrate 252 shown in FIGS. 5 and 6 or the separate substrate, but embodiments are not limited thereto. For example, the substrate 301 may be a transparent substrate.

The first electrode 305 may be disposed on the substrate 301. The activation layer 304 may be disposed on the first electrode 305. The second electrode may include at least one of a first or second sub-electrode 303, 307. The first sub-electrode 303 may be disposed on the substrate 301, the second sub-electrode 307 may be disposed on the activation layer 304 and be connected to the first sub-electrode 303.

In addition, as shown in FIGS. 8 and 9, the organic thin film photodiode 300 may further include a buffer layer 306 and a protective layer 302.

The buffer layer 306 may be disposed between the first electrode 305 and the activation layer 304. The protective layer 302 may be disposed on the second sub-electrode 307.

Hereinafter, a method for manufacturing the organic thin film photodiode shown in FIGS. 8 and 9 will be described.

First, the first electrode 305 may be formed on the pliable substrate 301, and then the buffer layer 306 and the activation layer 304 may be formed after surface treatment. Subsequently, the second electrode 303, 307 may be formed.

In addition, the second electrode may be configured as a single electrode, or may include a first sub-electrode 303 and a second sub-electrode 307.

The first sub-electrode 303 and the first electrode 305 may be formed on a substrate 301, which may take the form of glass.

The second sub-electrode 307 may be connected to the first sub-electrode 303 to serve as the second electrode and to protect the first sub-electrode 303 from oxidation/corrosion. In addition, the second sub-electrode 307 may be formed to include a material having a large difference in work function from the first sub-electrode 303. For example, the first sub-electrode 303 may be formed using LiF, and the second sub-electrode 307 may be formed using a material such as calcium (Ca) or aluminum (Al).

An indium tin oxide (ITO) pattern is designed and a mask is fabricated to form the first electrode 305 on the substrate 301 (or glass). The ITO, which represents indium tin oxide, is a commonly used conductive transparent electrode. The ITO is an oxide which presents a light-transmittable region in the visible light region and has high reflectance characteristic and a low electric resistance in the infrared light range. Further, in performing ITO patterning, a method of laser writer patterning or mask-applied patterning may be used.

Thereafter, the surface of the first electrode 305 is cleaned and subjected to hydrophilic treatment. For example, the cleaning operation may be performed using acetone and alcohol, and plasma treatment may be performed to secure a coatability. In this operation, a first step of sonication of a solution containing a detergent and distilled water, a second step of heating in an acetone solution, a third step of heating in an IPA solution, and a fourth step of UV-ozone treatment may be performed.

Thereafter, the buffer layer 306 may be formed on the first electrode 305. The buffer layer 306 may be formed by applying a coating of PEDOT:PSS (Poly Ethylene Thioophene:PolyStyrene Sulfonate) onto the first electrode 305. The PEDOT layer is a highly conductive polymer material and has excellent chemical stability such as light resistance and heat resistance. In addition, spin coating may be used in the printing process for forming the buffer layer 306. In this case, a first step of spin coating and a second step of baking on a hot plate may be performed.

Subsequently, the activation layer 304 may be formed. In this operation, an organic material used for the activation layer 304 may be synthesized and the activation layer 304 may be coated therewith. The activation layer 304 may be a layer that directly absorbs and senses light and may be formed using a printing process such as spin coating, ink jet printing, or slot die coating. In addition, the activation layer 304 may be formed using a fluorene-based polymer material or various other materials such as PC60BM and PC70BM.

In this operation, a first step of spin coating, a second step of baking on a hot plate, and a third step of removing the portion other than the activation region using acetone may be performed. In the case of preparing an activation layer solution, P3HT and PC60BM may be dissolved in a weight ratio of 1 to 0.7 in ODCB (1, 2-dichlorobenzene) and then be stirred.

After the activation layer 304 is formed, the second electrode 303, 307 may be formed. The second electrode 303, 307 may be formed through deposition to form a microelectrode. Deposition may be performed using a shadow mask. The second electrode 303, 307 may be formed using any material that is usable for electrodes, such as Ag, Ca/Ag or Al. Subsequently, an encapsulated glass layer may be formed. In this operation, an epoxy resin, which is an ultraviolet type resin, may be used. In addition, as described above, the second electrode may be configured as a single electrode or may include a first sub-electrode 303 and a second sub-electrode 307.

When the second electrode is formed, a first step of metal deposition of a LiF layer and an Al layer, a second step of annealing, and a third step of arranging a barrier layer on a glass layer, applying an ultraviolet (UV) resin to the glass layer and conducting UV treatment may be performed. In addition, in the case where the second electrode includes the first sub-electrode 303 and the second sub-electrode 307, the first sub-electrode 303 may be formed using LiF, and the second sub-electrode 307 may be formed using a material such as calcium (Ca) or aluminum (Al).

In this case, the first electrode 305 may be used as a positive electrode, and the second electrode 303, 307 may be used as a negative electrode. In addition, the difference in work function of the materials constituting the first electrode 305 and the second electrode 303, 307 may be 0.5 eV to 1.5 eV. The larger the difference in work function between the materials constituting the first electrode 305 and the second electrode 303, 307, the higher the efficiency.

Figure 10:
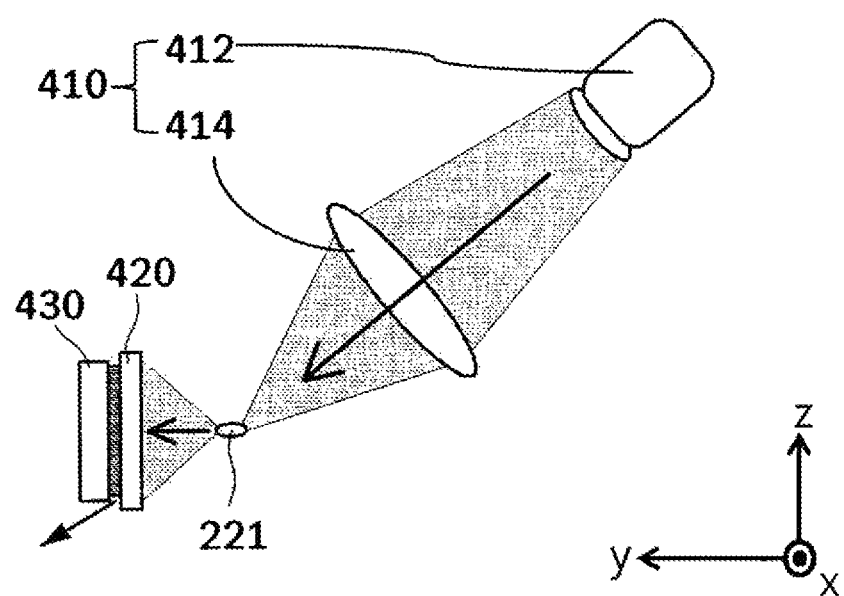
FIG. 10 is a cross-sectional view showing a particle sensing device according to another embodiment.

FIG. 10 is a cross-sectional view showing a particle sensing device 200C according to another embodiment.

The particle sensing device 200C shown in FIG. 10 may include a light emitter 410, a substrate 420, and a light receiver 430.

The description of the particle sensing devices 200A and 200B given above may be applied to the particle sensing device 200C shown in FIG. 10, unless specifically stated otherwise.

The light emitter 410 shown in FIG. 10 may perform the same function as the light emitter 210 shown in FIG. 2. In addition, the light emitter 410 may include a light source portion 412 and a light condenser 414. Here, the light source portion 412 and the light condenser 414 may perform the same functions as the light source portion 212 and the light condenser 214 shown in FIG. 2, respectively. Thus, redundant description of the light emitter 410, the light source portion 412, and the light condenser 414 shown in FIG. 10 will be omitted.

The light receiver 430 also plays the same role as the light receiver 230 shown in FIG. 2, and thus redundant description thereof will be omitted. In particular, the light receiver 430 may be implemented as an organic photodiode or a printed photodiode, as well as an organic thin film photodiode. When an organic photodiode is used as a material of the light receiver 430, the structure of the light receiver may be designed without restriction as to the area and shape thereof.

In the case where the light receiver 430 is formed in close contact with the substrate 420, the sensing distance to a target object becomes short, and thus the sensitivity of the light receiver 430 may be enhanced. In addition, since the sensing efficiency may be enhanced at a predetermined driving voltage compared to a conventional case, the same performance as in the conventional case may be realized at a low driving voltage.

Further, in the case where the light receiver 430 is not implemented using an organic thin film photodiode, a separate light condenser for condensing scattered light may be required. However, according to an embodiment, in the case of FIG. 10, the light emitter 410 includes the light condenser 414, while the light receiver 430 does not include a separate light condenser. This is because the organic photodiode that is disposed as the light receiver 430 on the transparent substrate 420 may perform the same function.

Preferably, the area of the light receiver is 1.5 times the area of the light condenser. Since there is no separate light condenser in the light receiver, the area of the light receiver may be increased as much as possible to receive the scattered light, thereby further increasing the efficiency of sensitivity.

In addition, the substrate 420 corresponds to the substrate 301 shown in FIG. 8 and performs the same function, and therefore redundant description thereof will be omitted. The substrate 420 may be a transparent substrate and may be disposed between the target object and the light receiver 430. The light receiver 430 may receive scattered light through the transparent substrate 420 and sense the target object. By forming the transparent substrate 420, the light receiver 430 may be prevented from being consumed or contaminated by direct contact with the outside. Therefore, the degree of sensing of the scattered light by the target object may be improved and maintenance of the light receiver 430 may be further facilitated. The substrate 420 may be flexible or rigid.

Similar to the case of FIG. 2, the particle sensing device 200C shown in FIG. 10 may emit and radiate light toward the particle 221, and the light receiver 430 may receive, through the substrate 420, the light scattered by the particle 221 and acquire information about the particle 221 using the received light.

As described above, when the light receiver 230, 230A, 230B, 230C, 430 is implemented using an organic thin film photodiode, the following effects may be obtained.

The thickness of the receiver may be reduced compared to the thickness of the conventional light receiver, and an efficient light receiver may be implemented with an area smaller than that of the conventional light receiver.

Further, the structure of the light receiver may be designed without restriction as to the area and shape thereof.

In addition, unlike a conventional case where each photodiode module is mounted on the silicon wafer, when the light receiver is implemented using an organic thin film photodiode as in the embodiments, the light receivers may be fabricated at once through a printing process, and accordingly the manufacturing time and processes may be shortened.

Further, since no separate light condenser is required on the side of the light receiver to condense light scattered by the particle 221, manufacturing costs may be reduced and a compact design may be realized.

The particle sensing devices 200A, 200B and 200C according to the embodiments described above may be applied to domestic and industrial air cleaners, air purifiers, air washers, air coolers, or air conditioners, or may be applied to air quality management systems for buildings, indoor/outdoor air conditioning systems for vehicles or indoor air quality measurement devices for vehicles. However, it should be noted that the particle sensing devices 200A and 200B according to the embodiments are not limited to these applications and may be applied to various fields.

The embodiments of the present disclosure described above are disclosed for the purpose of illustration, and the present disclosure is not limited thereto. It will be apparent to those skilled in the art that various modifications and variations may be made in the present disclosure without departing from the spirit and scope of the disclosure. Such modifications and variations should be understood as being within the scope of the present disclosure.

MODE FOR INVENTION

The mode for carrying out the disclosure has been fully described in "Best Mode".

INDUSTRIAL APPLICABILITY

The particle sensing devices according to embodiments may be applied to domestic and industrial air cleaners, air purifiers, air washers, air coolers, or air conditioners, or may be used in air quality management systems for buildings and indoor/outdoor air conditioning systems for vehicles or indoor air quality measurement devices for vehicles.

The invention claimed is:
1. A particle sensing device comprising:
a light emitter configured to emit and output light into a light scattering space;
a light receiver provided in a maximum light scattering angle region;
a substrate having the light receiver provided thereon;
a controller configured to analyze information on a particle using a photocurrent signal generated by the light receiver; and
a wire arranged to transmit the photocurrent signal generated by the light receiver to the controller,
wherein a maximum intensity of scattered light formed when the light emitted from the light emitter is scattered by the particle in the light scattering space is obtained in the maximum light scattering angle region,
wherein the light receiver is configured to receive the scattered light incident thereon and generate the photocurrent signal,
wherein the maximum light scattering angle region includes:
a first scattering region in a scattering angle range of 20° to 60° with respect to an optical axis of the light emitter; and
a second scattering region in a scattering angle range of −20° to −60° with respect to the optical axis of the light emitter,
wherein the light receiver includes:
an opening allowing the light emitted from the light emitter and passed through the light scattering space to be transmitted therethrough;
a first light receiving region provided in the first scattering region of the maximum light scattering angle region in a periphery of the opening; and
a second light receiving region provided in the second scattering region of the maximum light scattering angle region in the periphery of the opening, wherein the light receiver and the wire are provided on the substrate, wherein the substrate includes a pliable substrate, and wherein the first and second light receiving regions are provided around the opening on the pliable substrate to define the opening.

2. The particle sensing device according to claim 1, wherein the light emitter includes:

a light source; and a light condenser provided on the optical axis of the light source to condense light emitted from the light source.

3. The particle sensing device according to claim 1, wherein the first and second light receiving regions are on opposite sides of the opening, respectively, in a direction intersecting the optical axis.

4. The particle sensing device according to claim 1, wherein the first and second light receiving regions are connected to each other.

5. The particle sensing device according to claim 1, wherein a width of the opening is greater than a width of the first and second light receiving regions in a direction intersecting the optical axis.

6. The particle sensing device according to claim 1, wherein the first and second light receiving regions are separated from each other in a direction intersecting the optical axis.

7. The particle sensing device according to claim 1, wherein the light receiver has a concave cross-sectional shape having a constant curvature.

8. The particle sensing device according to claim 1, wherein the light receiver comprises an organic thin film photodiode.

9. The particle sensing device according to claim 8, wherein the organic thin film photodiode includes:

a first electrode provided on the substrate;

an activation layer provided on the first electrode; and a second electrode comprising at least one of a first sub-electrode or a second sub-electrode, wherein the first sub-electrode is provided on the substrate, and wherein the second sub-electrode is provided on the activation layer and is connected to the first sub-electrode.

10. The particle sensing device according to claim 9, wherein the organic thin film photodiode further includes:

a buffer layer provided between the first electrode and the activation layer; and a protective layer provided on the second sub-electrode.

11. The particle sensing device according to claim 1, further comprising:

a printed circuit board having the controller provided thereon.

12. The particle sensing device according to claim 1, wherein a portion of the pliable substrate corresponding to the opening is light-transmissive.

13. The particle sensing device according to claim 1, wherein a portion of the pliable substrate corresponding to the opening has a shape of a through hole.

14. The particle sensing device according to claim 13, further comprising:

an optical trap portion configured to trap light having passed through the through hole corresponding to the opening of the light receiver.

15. The particle sensing device according to claim 1, further comprising a housing configured to accommodate the light emitter and the light receiver and to form the light scattering space.

* * * * *